US006223750B1

(12) United States Patent
Ishikawa et al.

(10) Patent No.: US 6,223,750 B1
(45) Date of Patent: May 1, 2001

(54) URINARY INCONTINENCE TREATMENT INSTRUMENT

(75) Inventors: Norio Ishikawa; Shin Suda; Tadashi Sasaki; Hidehiro Hosaka, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/320,546

(22) Filed: May 27, 1999

(30) Foreign Application Priority Data

May 27, 1998 (JP) .................................................. 10-145381

(51) Int. Cl.[7] ....................................................... A61F 5/48
(52) U.S. Cl. .................. 128/885; 128/886; 128/DIG. 25; 600/13; 600/29
(58) Field of Search ................................... 128/885, 886, 128/DIG. 25; 600/29–31, 9–15

(56) References Cited

U.S. PATENT DOCUMENTS

| 5,036,859 | * | 8/1991 | Brown | 128/886 |
| 5,137,033 | * | 8/1992 | Norton | 128/886 |
| 5,725,471 | | 3/1998 | Davey et al. | 600/13 |
| 5,868,723 | * | 2/1999 | Al-Sabah | 128/886 |
| 5,984,854 | | 11/1999 | Ishikawa et al. | 600/9 |

FOREIGN PATENT DOCUMENTS

| 93 00 499 U | 3/1993 | (DE) . |
| 5 501 048 U | 9/1992 | (EP) . |
| 0 788 813 | 8/1997 | (EP) . |
| 0 850 665 | 7/1998 | (EP) . |
| 09276418 | 10/1997 | (JP) . |
| 9-276418 | * 10/1997 | (JP) . |
| WO 95 27533 | 10/1995 | (WO) . |

* cited by examiner

Primary Examiner—Michael A. Brown
(74) Attorney, Agent, or Firm—Sughrue, Mion, Zinn, Macpeak & Seas, PLLC

(57) ABSTRACT

A seat face part 20 of a chair 1 is provided with a stimulating coil 3. A projection 10 is made on the top of the stimulating coil 3. When a treated patient sits in the chair 1, the anus of the treated patient is placed on the top of the projection 10, whereby the treated patient can be made to sit at the optimum position for urinary incontinence treatment relative to the stimulating coil 3.

9 Claims, 7 Drawing Sheets

URINARY INCONTINENCE TREATMENT INSTRUMENT

BACKGROUND OF INVENTION

1. Field of Invention

This invention relates to a urinary incontinence treatment instrument for applying a magnetic line of force to a treated patient for urinary incontinence treatment.

2. Related Art

A urinary incontinence treatment apparatus with a magnetic stimulating coil buried in a chair is shown, for example, in JP-A-9-276418. According to such an apparatus, urinary incontinence treatment is conducted in the same state as a patient sits in a normal chair, so that easy treatment can be conducted without burdening the treated patient or the operator with the treatment.

In magnetic stimulating intended for urinary incontinence treatment, an eddy current is produced in a living body by a fluctuating magnetic field for stimulating the pelvic floor muscle or pudendal nerve from urethral opening to the anus or perineum neighborhood. At this time, to suppress power consumption, it is necessary to efficiently give an effective stimulus to the parts.

In the apparatus in the related art, if the treated patient sits in a treatment chair, generally a magnetic line of force is applied to the portion from the femoral region to the buttocks of the treated patient; the apparatus does not efficiently give an effective stimulus.

SUMMARY OF INVENTION

It is therefore an object of the invention to efficiently generate an eddy current at the part of a treated patient to be stimulated in urinary incontinence treatment.

According to a first aspect of the present invention, there is provided a urinary incontinence treatment instrument comprising a magnetic stimulating coil, a magnetic stimulating coil support section for supporting the magnetic stimulating coil, the magnetic stimulating coil support section comprising an abutment face for abutting the buttocks and the femoral region of a treated patient on the periphery of the magnetic stimulating coil, and sense means for causing a treated patient to sense that the treated patient abuts the abutment face in a predetermined state. According to the urinary incontinence treatment instrument, the treated patient can be made to sense whether or not the magnetic stimulating coil is placed at a proper position.

In the present invention, in the urinary incontinence treatment instrument, the sense means is a projection made on the top of the magnetic stimulating coil. Thus, the treated patient can sense whether or not the magnetic stimulating coil is placed at a proper position in response to the touch of the projection.

In the present invention, in the urinary incontinence treatment instrument, a notch for inserting a micturition checker is made at the front center of the abutment face of the magnetic stimulating coil support section. Thus, the checking person can insert a micturition checker through the notch.

In the present invention, in the urinary incontinence treatment instrument, the portion of the abutment face placed at the position of the crotch of the treated patient in a state in which the buttocks and the femoral region of the treated patient abut the abutment face is shaped like a protrusion. Thus, when the instrument is used, the treated patient is placed in a position sitting astride the instrument.

In the present invention, in the urinary incontinence treatment instrument, the sense means is an abutment face having a recess shaped so as to accept the buttocks and the femoral region of the treated patient. Thus, the treated patient can sense whether or not the magnetic stimulating coil is placed at a proper position in response to the abutment feel of the buttocks and the femoral region against the abutment face.

In the present invention, in the urinary incontinence treatment instrument, the recess is shaped like two grooves for accepting the buttocks and the femoral region of the treated patient so that the treated patient is placed in a position sitting astride the instrument. Thus, when the instrument is used, the treated patient is placed in a position sitting astride the instrument.

In the present invention the urinary incontinence treatment instrument further includes means being placed on the periphery of the magnetic stimulating coil or the outer surface thereof for cutting off or preventing a sound produced from the magnetic stimulating coil. Thus, the sound produced from the magnetic stimulating coil is cut off or prevented.

In the present invention, in the urinary incontinence treatment instrument, the magnetic stimulating coil is shaped like a saddle bent so as to fit to the abutment part of the treated patient. Thus, the magnetic stimulating coil fits to the abutment part of the treated patient and the magnetic stimulating coil and the treated patient can be brought into intimate contact with each other.

DETAILED DESCRIPTION OF THE PREFERRED EMBODIMENTS

Figure 1:
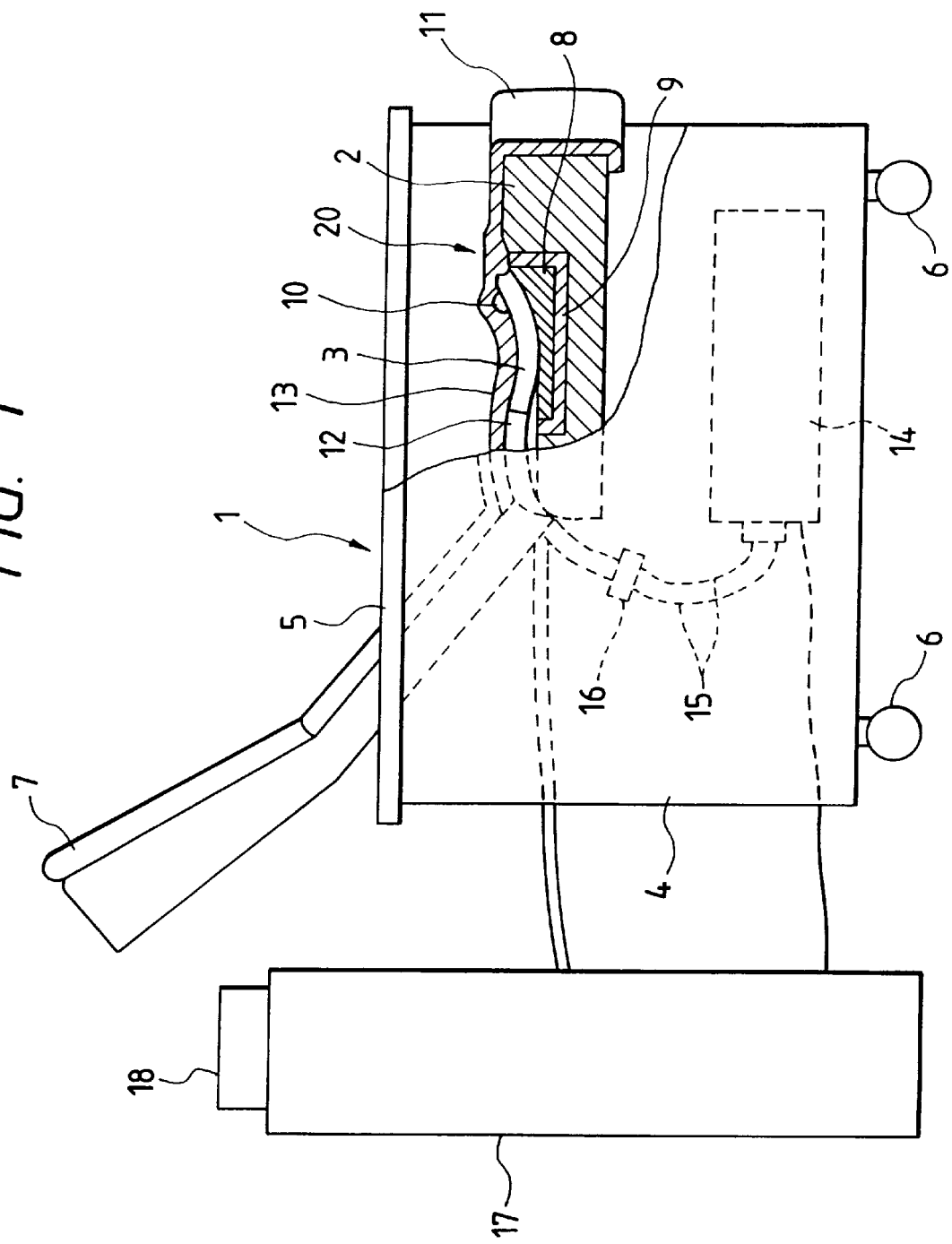
FIG. 1 is a drawing to show a general configuration of an embodiment of the invention.

FIG. 1 is a drawing to show a general configuration of a urinary incontinence treatment system using a urinary incontinence treatment instrument of the invention. In the example, the urinary incontinence treatment instrument is of a chair type wherein a seat plate 2 of a chair 1 is provided with a stimulating coil 3 and a pulse current is supplied to the stimulating coil 3 for generating a magnetic flux, thereby producing an eddy current on a living body for urinary incontinence treatment. The seat plate 2 is supported between a pair of foot parts 4 formed each like a box. The stimulating coil 3 is housed in a sound-proof box 9 containing a sound insulating material 8. The stimulating coil 3 is formed on the front top with a projection 10. The seat plate 2 is formed at the front center with a notch 11 for inserting a micturition device. The top and the front of the seat plate 2 provided with the stimulating coil 3 are covered with a cushion member 12 and furthermore covered with a seat member 13. The seat plate 2, the cushion member 12, and the seat member 13 make up a seat face part 20 (magnetic stimulating coil support part).

A cooling unit 14 is placed below the seat plate 2. The stimulating coil 3 is formed of a steel pipe. The stimulating coil 3 and the cooling unit 14 are connected by a cooling tube 15 so that cooling water or any other refrigerant is circulated in the stimulating coil 3. The structure of the stimulating coil 3 will be discussed later in detail. The cooling tube 15 is a Teflon tube having an insulating characteristic and is connected to the steel pipe forming the stimulating coil 3 by a one-touch connection tool 16 having an insulating characteristic. To introduce cooling water or any other refrigerant, the portion of the steel pipe projecting from the stimulating coil 3 and the cooling tube 15 are covered on the surfaces with a heat insulating material. To provide an electric insulating characteristic, glass fiber tape is wound around the surface of the stimulating coil 3 and furthermore the stimulating coil 3 is cured with insulating resin epoxy. The projection 10 is placed thereon.

An armrest 5 is provided on the top of the foot part 4. A pair of wheels 6 each with a stopper is attached on the bottom of each foot part 4. A chair back 7 is provided on the rear end of the seat plate 2.

The stimulating coil 3 and the cooling unit 14 are connected to a power supply section 17. A control unit 18 is placed on the top of a cabinet of the power supply section 17. The power supply section 17 is connected to a commercial power supply and supplies necessary electric power to the stimulating coil 3 and the cooling unit 14 under the control of the control unit 18. Here, for example, the circuit of coil feeding means shown in JP-A-9-276418 is used as a circuit feeding power into the stimulating coil 3.

Figure 2:
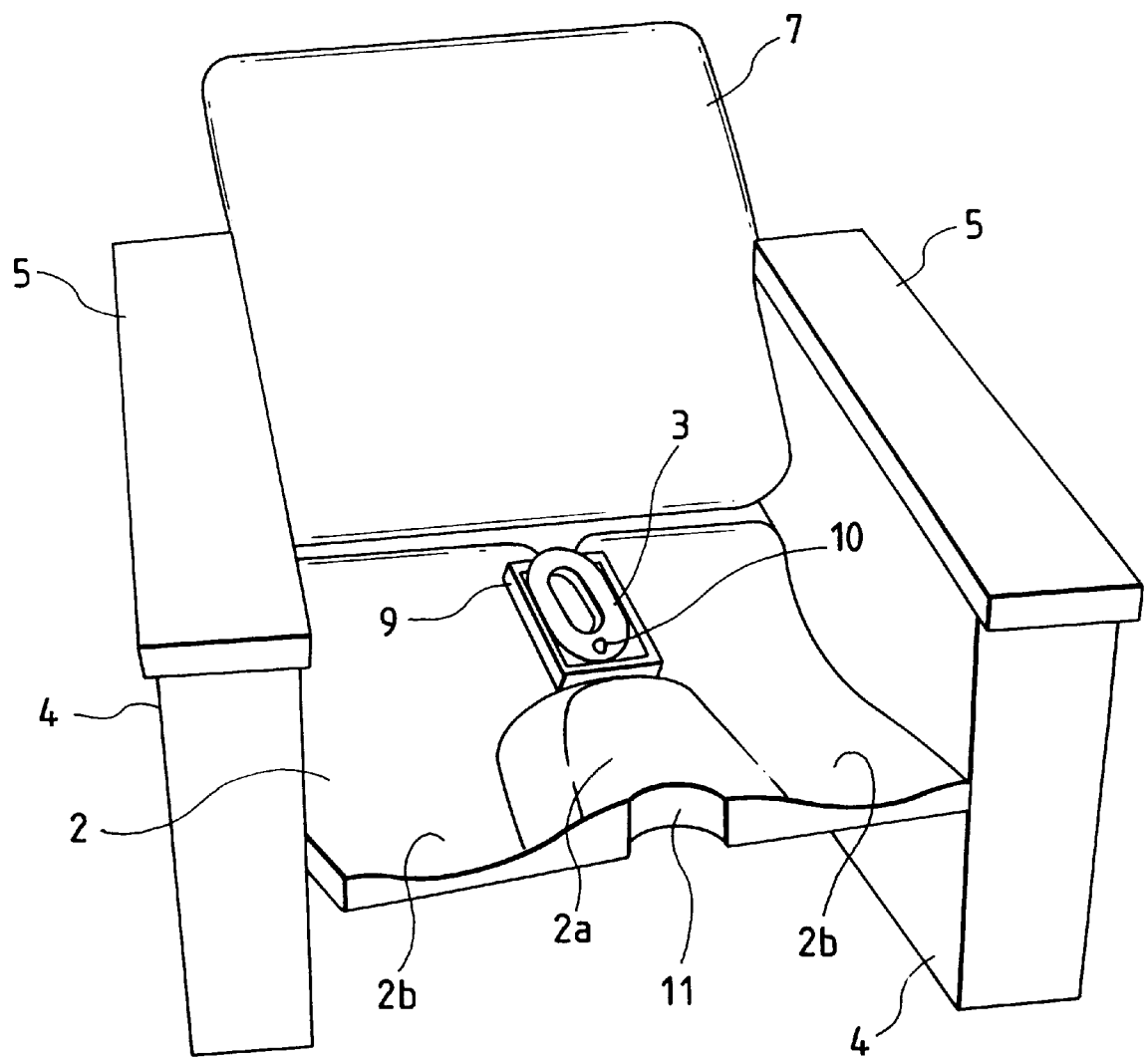
FIG. 2 is a perspective view of a chair 1 shown in FIG. 1 seeing it from ahead.
Figure 3:
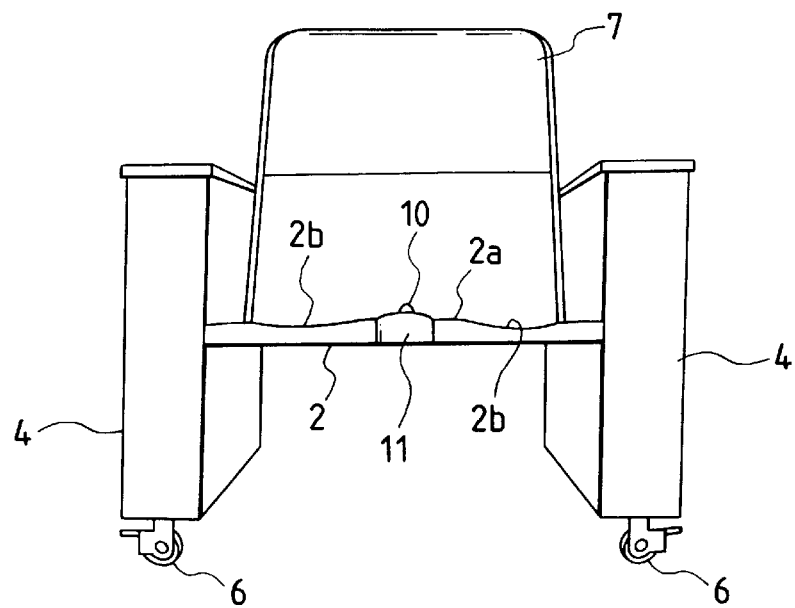
FIG. 3 is a front view of the chair 1 shown in FIG. 1.
Figure 4:
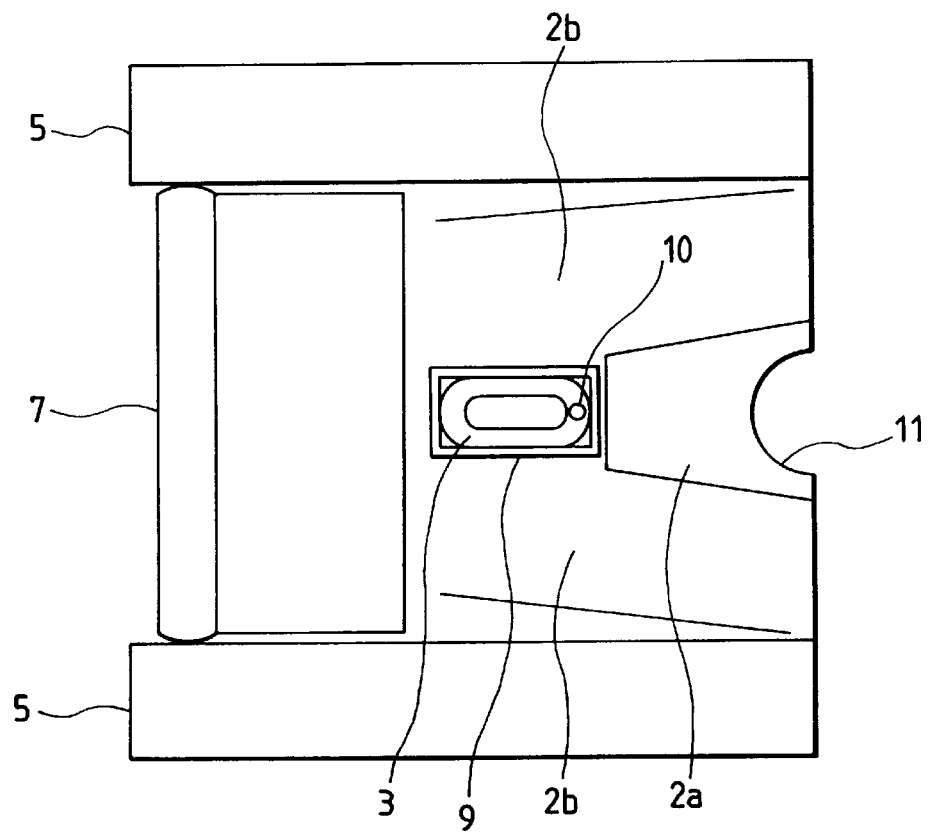
FIG. 4 is a plan view of the chair 1 shown in FIG. 1.
Figure 5:
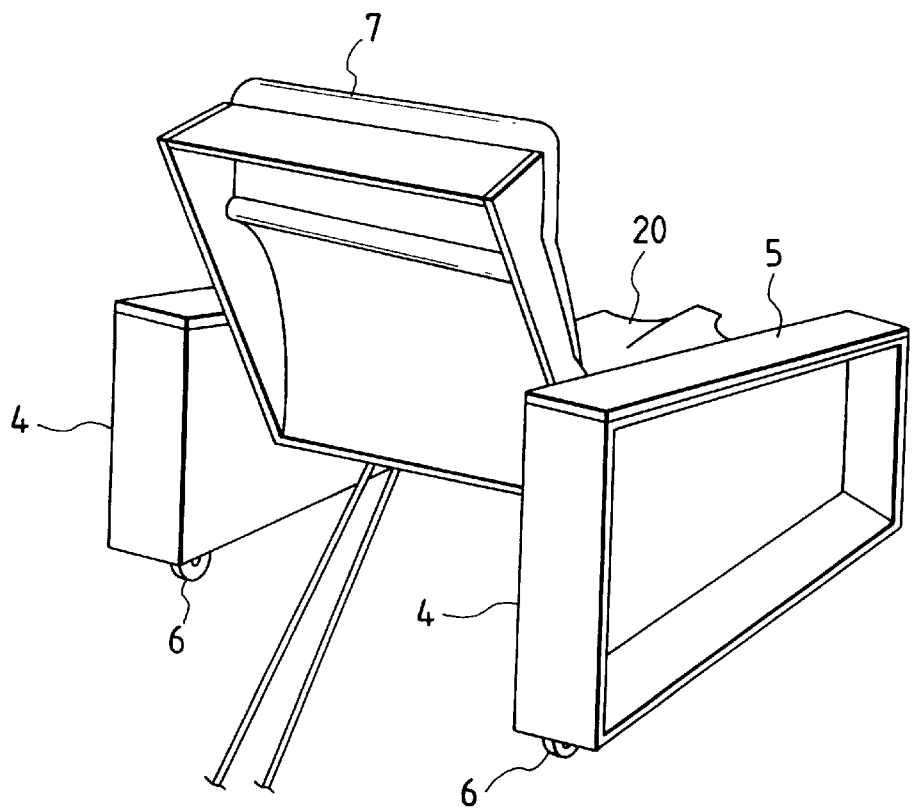
FIG. 5 is a perspective view of the chair 1 shown in FIG. 1 seeing it from behind.
Figure 10:
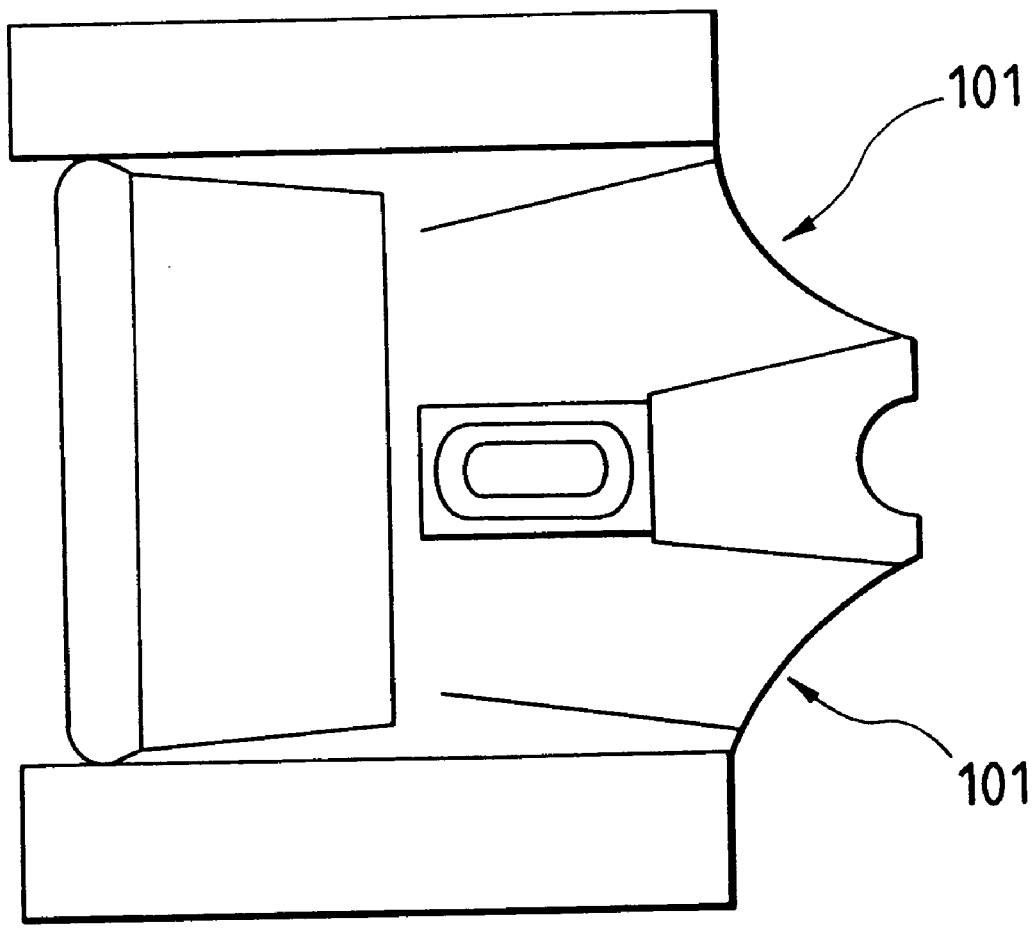
FIG. 10 as a plan view of the embodiment of the present invention.

FIGS. 2 to 4 are a perspective view, a front view, and a plan view of the chair 1 in a state in which the cushion member 12 and the seat member 13 are removed to show in detail the position of the stimulating coil 3 and the shape of the seat plate 2 shown in FIG. 1. As shown in FIGS. 2 to 4, the stimulating coil 3 is placed from the center of the seat plate 2 to the rear thereof and the portion of the chair 2 from the front to the rear is a protrusion 2a. In the seat plate 2, recesses 2b are formed back and forth on both sides sandwiching the protrusion 2a and the stimulating coil 3. The seat face part 20 comprising the seat plate 2 covered with the cushion member 12 and the seat member 13 is formed with the protrusion and the recesses. When a treated patient sits in the chair 1, the crotch of the treated patient is positioned at the protrusion 2a. The recesses are formed so as to fit to the buttocks and femoral region of the treated patient. As seen in the plan view of FIG. 4, a pair of the recesses 2b is shaped like grooves and the recesses 2b fall apart from each other toward the front of the seat plate 2 so that the treated patient naturally places the legs astride when the treated patient sits in the chair 1. As shown in FIG. 10, it is applicable for employing a cut out portion 101 which is provided on both front contact sides of the seat plate 2. Upon this structure, the treated patient could sit under the condition that the femoral region moves toward the chair back 7 as much as possible, and the buttocks of the treated patient is closely fitted on the seat plate having the recesses. As a result, the distance between the buttocks and the stimulating coil 3 could be minimized as much as possible so that the efficiency of magnetic stimulating is enhanced at the high density of the eddy current generated in the living body. Additionally, it is better to employ the width of seat plate which is not exceedingly wider than the back. FIG. 5 is a perspective view seeing the chair 1 diagonally from behind.

Figure 6:
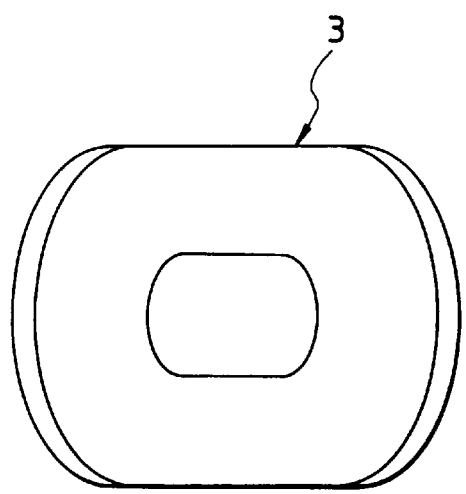
FIG. 6 is a plan view of a stimulating coil 3 shown in FIG. 1.
Figure 7:
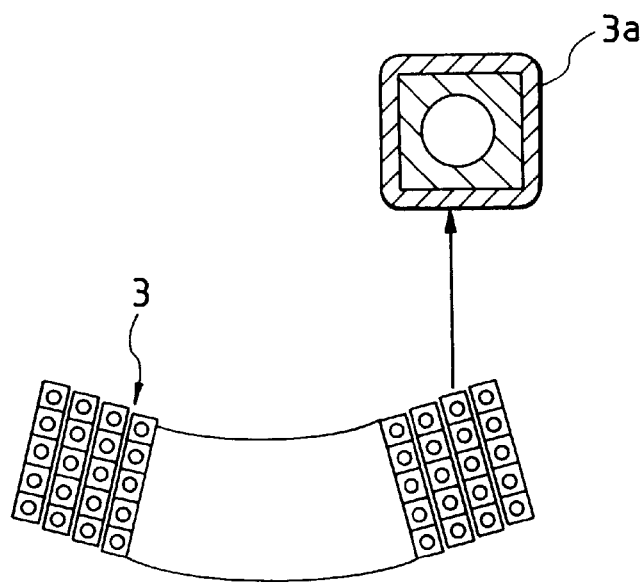
FIG. 7 is a longitudinal sectional view of the stimulating coil 3 shown in FIG. 1.

FIGS. 6 and 7 are a plan view and a longitudinal sectional view of the stimulating coil 3 respectively. As shown in the figures, the stimulating coil 3 warps up at both ends in the length direction of the stimulating coil 3 and is bent on the whole as a saddle. As described above, the stimulating coil 3 comprises a steel pipe wound as shown in FIG. 7. A part of FIG. 7 is an enlarged view of one section of the steel pipe, and numeral 3a denotes polyurethane of a sound insulating material.

Figure 8:
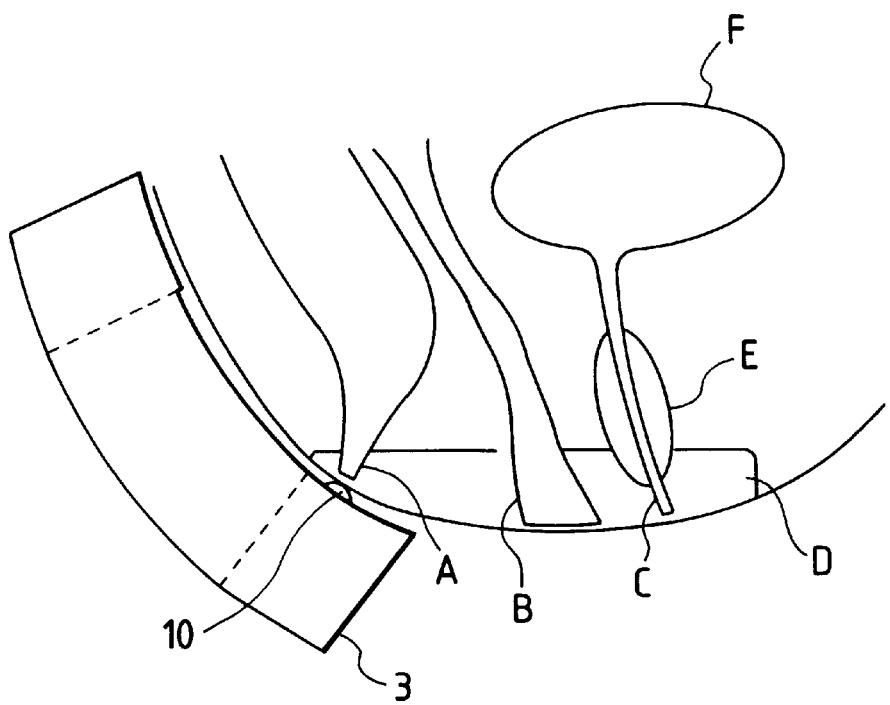
FIG. 8 is a drawing to describe the positional relationship between the stimulating coil 3 shown in FIG. 1 and a living body.

Next, the operation of the described system will be discussed. First, the treated patient sits on the seat face part 20 with clothes on and puts the back on the chair back 7. At this time, the buttocks and femoral region of the treated patient are fitted to the recesses of the seat face part 20 and the protrusion of the seat face part 20 is placed at the position of the crotch of the treated patient. Thus, the feet of the treated patient naturally open and the stimulating coil 3 abuts the portion of the treated patient from the anus to the rear thereof. Further, if the treated patient is previously instructed to place the anus just above the projection 10 on the stimulating coil 3, the treated patient sits at a previously assumed position more accurately. Thus, the stimulating coil 3 is placed at the optimum position for the treated patient. FIG. 8 shows a state in which the stimulating coil 3 abuts the treated patient properly. However, clothes of the treated patient and the cushion member 12 and the seat member 13 of the chair 1 are not shown to clearly show the relationship between the stimulating coil 3 and the treated patient. In the figure, letter A denotes an anus, letter B denotes a vagina, letter C denotes a urethra, letter D denotes a pelvic floor muscle and pudendal nerve, letter E denotes an external urethral sphincter, and letter F denotes a urinary bladder.

Next, the operator operates the control unit 18 to set magnetic stimulating conditions. Here, the magnetic stimulating conditions are the repetitive frequency of a generated magnetic field (frequency of electric current supplied to the stimulating coil 3), the stimulating strength (magnitude of the electric current), the stimulating time (time for which the stimulating coil is driven), etc. Next, the operator operates the control unit 18 to turn on the power supply section 17.

Resultantly, a fluctuating magnetic field is generated from the stimulating coil 3 and an eddy current induced by the generated fluctuating magnetic field flows into the pelvic floor muscle or pudendal nerve of the treated patient. Here, since the stimulating coil 3 is at the optimum position for the treated patient, an effective stimulus can be added to the treated patient efficiently.

On the other hand, the cooling unit 14 also operates for circulating cooling water or any other refrigerant in the stimulating coil 3, thereby preventing the stimulating coil 3 from becoming a high temperature. The sound insulating material 8 and the sound-proof box 9 prevent a sound produced from the stimulating coil 3 from reaching the outside so as not to give the treated patient an unpleasant feeling caused by noise produced at the treatment time.

Figure 9A:
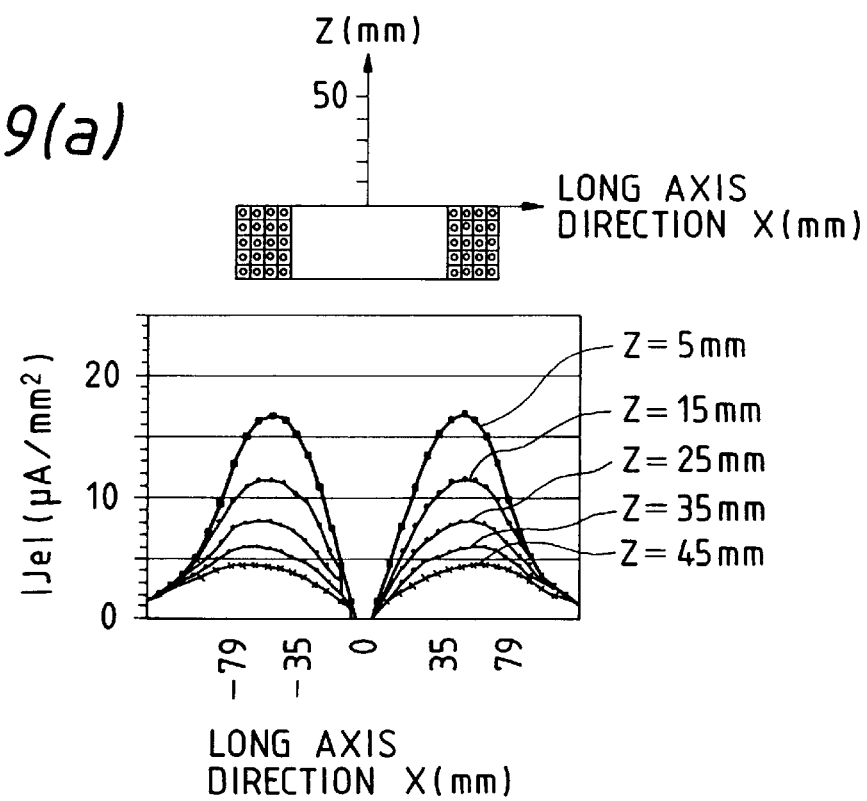
FIGS. 9(a) and 9(b) are drawings to describe the function of the stimulating coil 3 shown in FIG. 1.
Figure 9B:
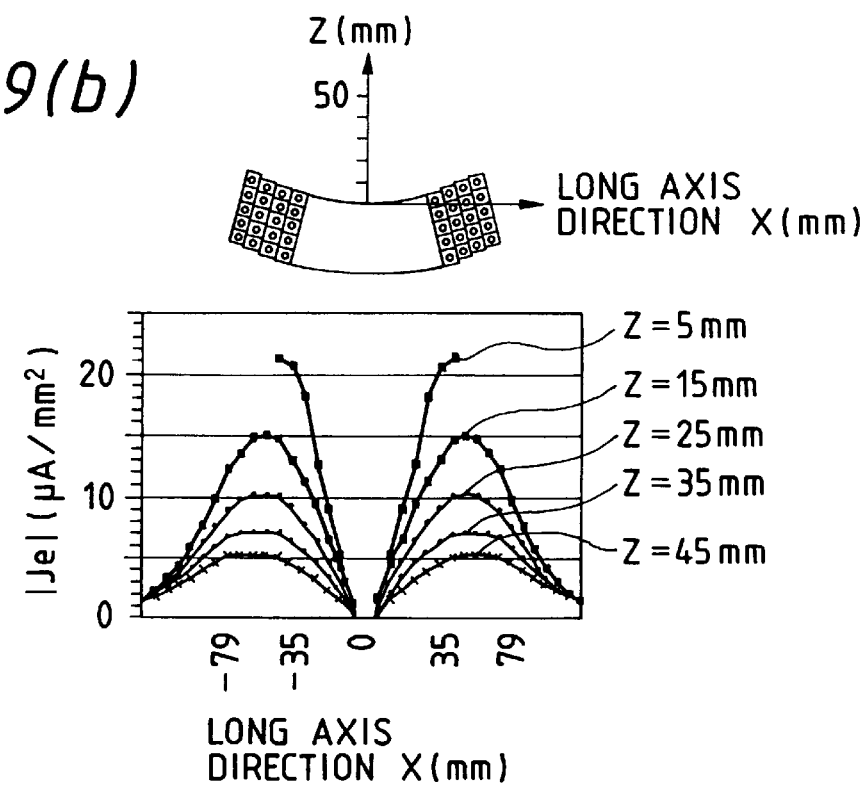

In the embodiment, the stimulating coil 3 is bent as shown in FIG. 9B, and has a curvature matched with the curvature of the neighborhood of the anus of a human being (female). Thus, the distance between the surface of the stimulating coil 3 and a living body can be made very small, so that the stimulating coil 3 can generate a large eddy current in the depth of the living body.

FIG. 9A shows a flat stimulating coil with no bend. If an attempt is made to stimulate the neighborhood of an anus of a living body with such a flat stimulating coil, a large eddy current cannot be generated in the depth of the living body since the distance between the coil surface and the living body is large.

As shown in FIG. 9, the eddy current density is zero on the center axis of the stimulating coil and reaches the maximum in the vicinity of an intermediate position of the inner diameter and the outer diameter of the coil. If a part with a large eddy current density is the part to simulate, a stimulus can be given with low power consumption. Then, in the embodiment, the stimulating coil 3 is formed on the top with the projection 10.

If the treated patient sits in the chair so as to place the anus on the projection 10, the anus neighborhood is most stimulated. Stimulating the anus leads to an extreme effect produced on urinary incontinence treatment. Thus, urinary incontinence treatment can be conducted with low power consumption. According to the embodiment, power consumption which was formerly about 3 kW can be reduced to 2 kW or less.

In the embodiment, the recesses are made in the seat face part 20 and the projection 10 is made on the stimulating coil as means for causing the treated patient to sense that the stimulating coil 3 is placed at a proper position. The projection 10 may contain a spring for providing elasticity.

In place of the sensing means, an electrode may be provides at any point of the chair 1 abutting the treated patient for giving an electric stimulus to the treated patient for causing the treated patient to sense whether or not the treated patient sits at a proper position. A nozzle for jetting air may be provided at any point of the chair 1 for causing the treated patient to sense whether or not the treated patient sits at a proper position by jetting air. A heating element or a heat absorption element may be placed at any point of the chair 1 for causing the treated patient to sense whether or not the treated patient sits at a proper position according to the temperature of the element.

In the embodiment, the seat plate 2 and the chair back 7 are fixed to the foot parts 4; however, if a structure is adopted wherein the seat plate 2 and the chair back 7 can be changed at angles relative to the foot parts 4 as desired, the seat face part 20 can be abutted against the treated patient in a more appropriate condition in response to the treated patient. The embodiment provides the urinary incontinence treatment instrument using the chair, but the urinary incontinence treatment instrument may not be of chair type if it causes the treated patient to sense whether or not the stimulating coil is placed at a proper position. A similar advantage can be provided, for example, if the urinary incontinence treatment instrument of the type wherein the seat face part 20 is detached from the chair 1 is used for the treated patient lying in bed.

According to the present invention, an effective stimulus can be added to the treated patient efficiently, so that treatment can be conducted with low power consumption. Thus, the urinary incontinence treatment instrument can be used in general hospitals and further in general homes. Since only the target part can be stimulated and the fear of stimulating any other part than the target is eliminated, safety can be provided.

According to the present invention, the treated patient can be informed of the proper position for the stimulating coil according to the extremely simple configuration.

According to the present invention, the checking person can conduct a micturition check easily.

According to the present invention, the treated patient can be placed in a position fitted to treatment.

According to the present invention, the treated patient can sense in a natural posture whether or not the magnetic stimulating coil is placed at a proper position.

According to the present invention, the treated patient can be placed easily in a position fitted to treatment, namely, a position sitting astride the instrument.

According to the present invention, the sound produced from the magnetic stimulating coil can be cut off or prevented, so that an unpleasant feeling caused by noise is not given to the treated patient.

According to the present invention, the magnetic stimulating coil and the treated patient can be brought into intimate contact with each other, thus a stimulus can be given to the treated patient efficiently.

What is claimed is:

1. An incontinence treatment instrument comprising:
   a magnetic stimulating coil;
   a magnetic stimulating coil support section for supporting said magnetic stimulating coil, said magnetic stimulating coil support section including an abutment face for abutting buttocks and a femoral region of a treated patient on a periphery of said magnetic stimulating coil; and
   a notifying mechanism which notifies a treated patient to a condition that the treated patient abuts the abutment face in a predetermined state.

2. The incontinence treatment instrument as claimed in claim 1, wherein said notifying mechanism comprises a projection made on the top of said magnetic stimulating coil.

3. An incontinence treatment instrument comprising:
   a magnetic stimulation coil; and
   a magnetic stimulation coil support section for supporting said magnetic stimulation coil, said magnetic stimulation coil support section including an abutment face for abutting buttocks and a femoral region of a treated patient on a periphery of said magnetic stimulation coil,
   wherein a notch for inserting a micturition checker is made at the front center of the abutment face of said magnetic stimulating coil support section.

4. An incontinence treatment instrument comprising:
   a magnetic stimulation coil; and
   a magnetic stimulation coil support section for supporting said magnetic stimulation coil, said magnetic stimulation coil support section including an abutment face for abutting buttocks and a femoral region of a treated patient on a periphery of said magnetic stimulation coil,
   wherein a portion of said abutment face placed at a position of a crotch of a treated patient in a state in which the buttocks and the femoral region of the treated patient abut said abutment face is shaped like a protrusion.

5. An incontinence treatment instrument comprising:
   a magnetic stimulation coil; and
   a magnetic stimulation coil support section for supporting said magnetic stimulation coil, said magnetic stimulation coil support section including an abutment face for abutting buttocks and a femoral region of a treated patient on a periphery of said magnetic stimulation coil,
   wherein said abutment face has a recess shaped so as to accept the buttocks and the femoral region of the treated patient.

6. The incontinence treatment instrument as claimed in claim 5 wherein the recess is shaped like two grooves for accepting the buttocks and the femoral region of the treated patient so that the treated patient is placed in a position sitting astride said instrument.

7. An incontinence treatment instrument comprising:

a magnetic stimulation coil; and a magnetic stimulation coil support section for supporting said magnetic stimulation coil, said magnetic stimulation coil support section including an abutment face for abutting buttocks and a femoral region of treated patient on the periphery of said magnetic stimulation coil, means for at least cutting off and preventing a sound produced from said magnetic stimulation coil or the outer surface thereof.

8. An incontinence treatment instrument comprising:

a magnetic stimulation coil; and a magnetic stimulation coil support section for supporting said magnetic stimulation coil, said magnetic stimulation coil support section including an abutment face for abutting buttocks and a femoral region of a treated patient on a periphery of said magnetic stimulation coil, wherein said magnetic stimulation coil is shaped like a saddle bent so as to fit to an abutting portion of the treated patient.

9. An incontinence treatment instrument comprising:

a magnetic stimulation coil; and a magnetic stimulation coil support section for supporting said magnetic stimulation coil, said magnetic stimulation support section including an abutment face for abutting buttocks and a femoral region of a treated patient on a periphery of said magnetic stimulation coil, wherein said abutment face has two recesses for positioning the treated patient.

* * * * *